United States Patent [19]

Boehm

[11] Patent Number: 5,196,203
[45] Date of Patent: Mar. 23, 1993

[54] THEOPHYLLINE DOSAGE FORM

[75] Inventor: Garth Boehm, Adelaide, Australia

[73] Assignee: F. H. Faulding & Co. Limited, Salisbury South, Australia

[21] Appl. No.: 767,342

[22] Filed: Sep. 27, 1991

Related U.S. Application Data

[63] Continuation of Ser. No. 457,198, Dec. 29, 1989, abandoned.

[30] Foreign Application Priority Data

Jan. 6, 1989 [AU] Australia .............................. PJ2191

[51] Int. Cl.$^5$ .......................... A61K 9/24; A61K 9/58
[52] U.S. Cl. .................................... 424/469; 424/461; 424/462; 424/468; 424/490; 424/493; 424/494; 424/495; 424/497
[58] Field of Search ............... 424/497, 461, 462, 490, 424/617, 682, 468, 493–495

[56] References Cited

U.S. PATENT DOCUMENTS

| | | | |
|---|---|---|---|
| 4,083,949 | 4/1978 | Benedikt | 424/19 |
| 4,367,217 | 1/1983 | Gruber et al. | 424/19 |
| 4,415,547 | 11/1983 | Yu et al. | 424/19 |
| 4,587,118 | 5/1986 | Hsiao | 424/19 |
| 4,661,162 | 4/1987 | Kurihara et al. | 106/169 |
| 4,708,874 | 11/1987 | Haan et al. | 424/470 |
| 4,713,248 | 12/1987 | Kjorn et al. | 424/458 |
| 4,786,509 | 11/1988 | Chang et al. | 424/490 |
| 4,800,087 | 1/1989 | Mehta | 424/497 |
| 4,803,080 | 2/1989 | Benedik et al. | 424/488 |
| 4,844,910 | 7/1989 | Leslie et al. | 424/494 |
| 4,851,228 | 7/1989 | Zentner et al. | 424/456 |

FOREIGN PATENT DOCUMENTS

| | | |
|---|---|---|
| 4323685 | 3/1985 | Australia . |
| 51460/85 | 7/1986 | Australia . |
| 68206 | 8/1987 | Australia . |
| 81997/87 | 6/1988 | Australia . |
| 0164959 | 5/1985 | European Pat. Off. . |
| 0260236 | 3/1988 | European Pat. Off. . |
| 0270305 | 6/1988 | European Pat. Off. . |
| 0287536 | 10/1988 | European Pat. Off. . |
| 0327295 | 1/1989 | European Pat. Off. . |
| 1568837 | 6/1980 | United Kingdom . |
| 2101069 | 1/1983 | United Kingdom . |

Primary Examiner—Thurman K. Page
Assistant Examiner—G. S. Kishore
Attorney, Agent, or Firm—Darby & Darby

[57] ABSTRACT

A pH-dependent sustained release pharmaceutical pellet composition and a method of administering the same to a patient at a predetermined dosage and interval, said pellet composition comprising: a core element containing a therapeutically effective amount of theophylline, xanthine or a derivative thereof as the active ingredient and a coating on said core element which comprises the following components:

(a) at least 40% of a matrix polymer which is insoluble at a pH of from 1 to 7.5 and contributes to the control of the rate of release of the active ingredient in the stomach and intestines;

(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;

(c) from 1 to 60% of a compound soluble at a pH of from 1 to 4, sufficient to enable initiation of release of the active ingredient in the stomach;

said percentages being by weight based on total weight of components (a), (b), and (c); the ratio of the components (a), (b), and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of said active ingredient over the course of said predetermined interval, said coated core element having a diameter of from 510 to 2400 microns.

14 Claims, 4 Drawing Sheets

Figure 1: Dissolution Profile for Pellet Composition B
(Average Data for 6 Samples)

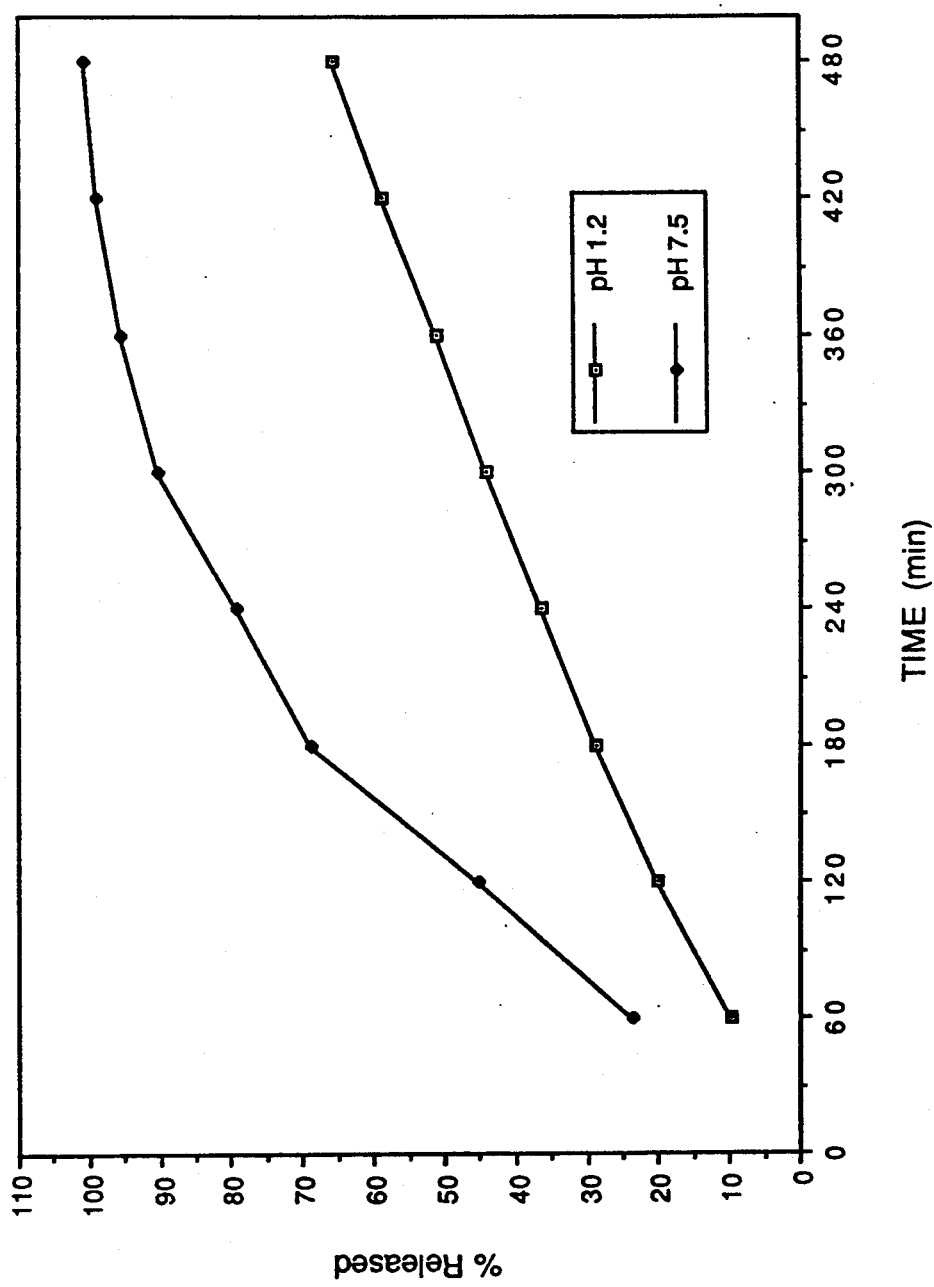
Figure 1: Dissolution Profile for Pellet Composition B
(Average Data for 6 Samples)

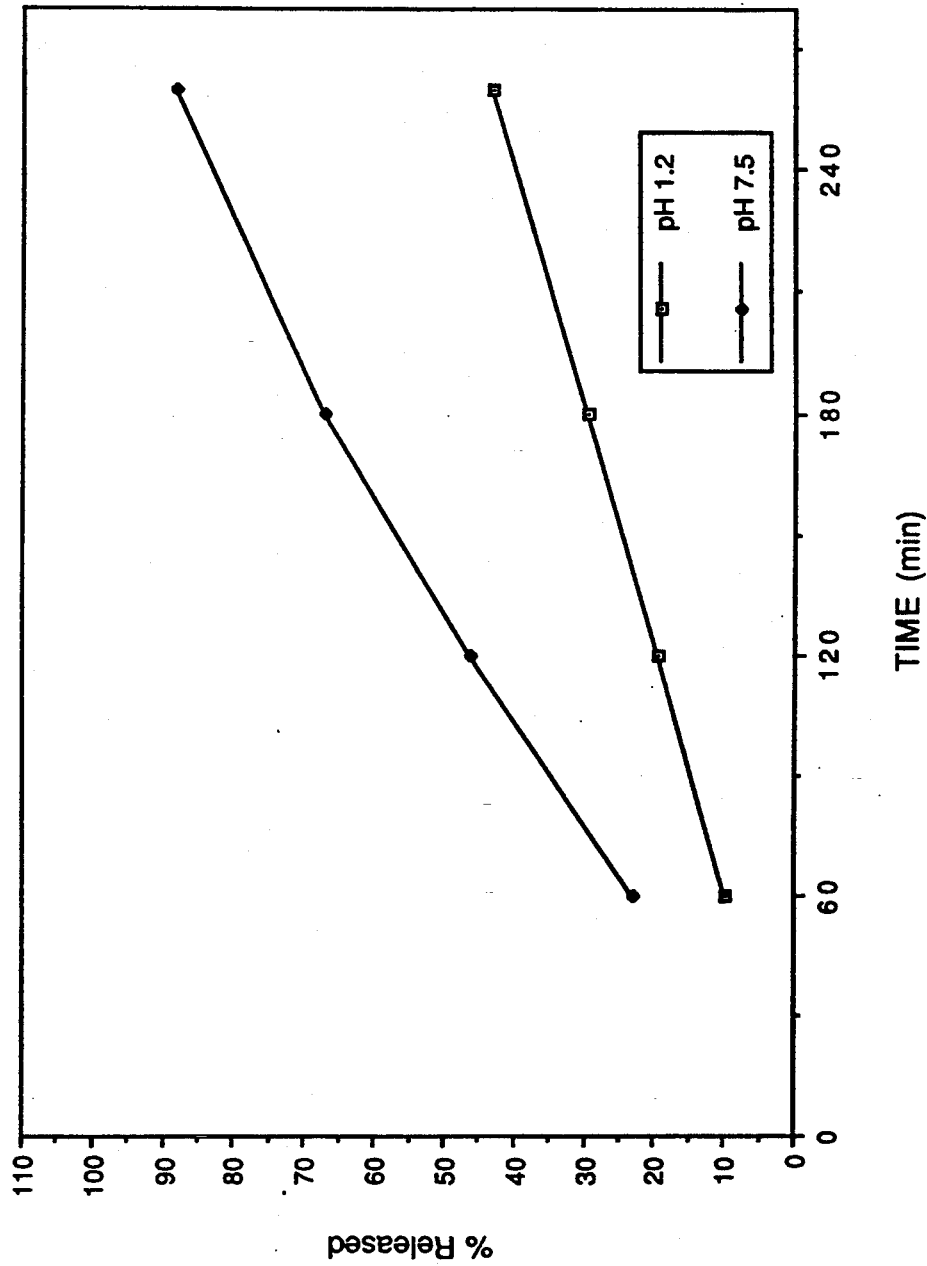

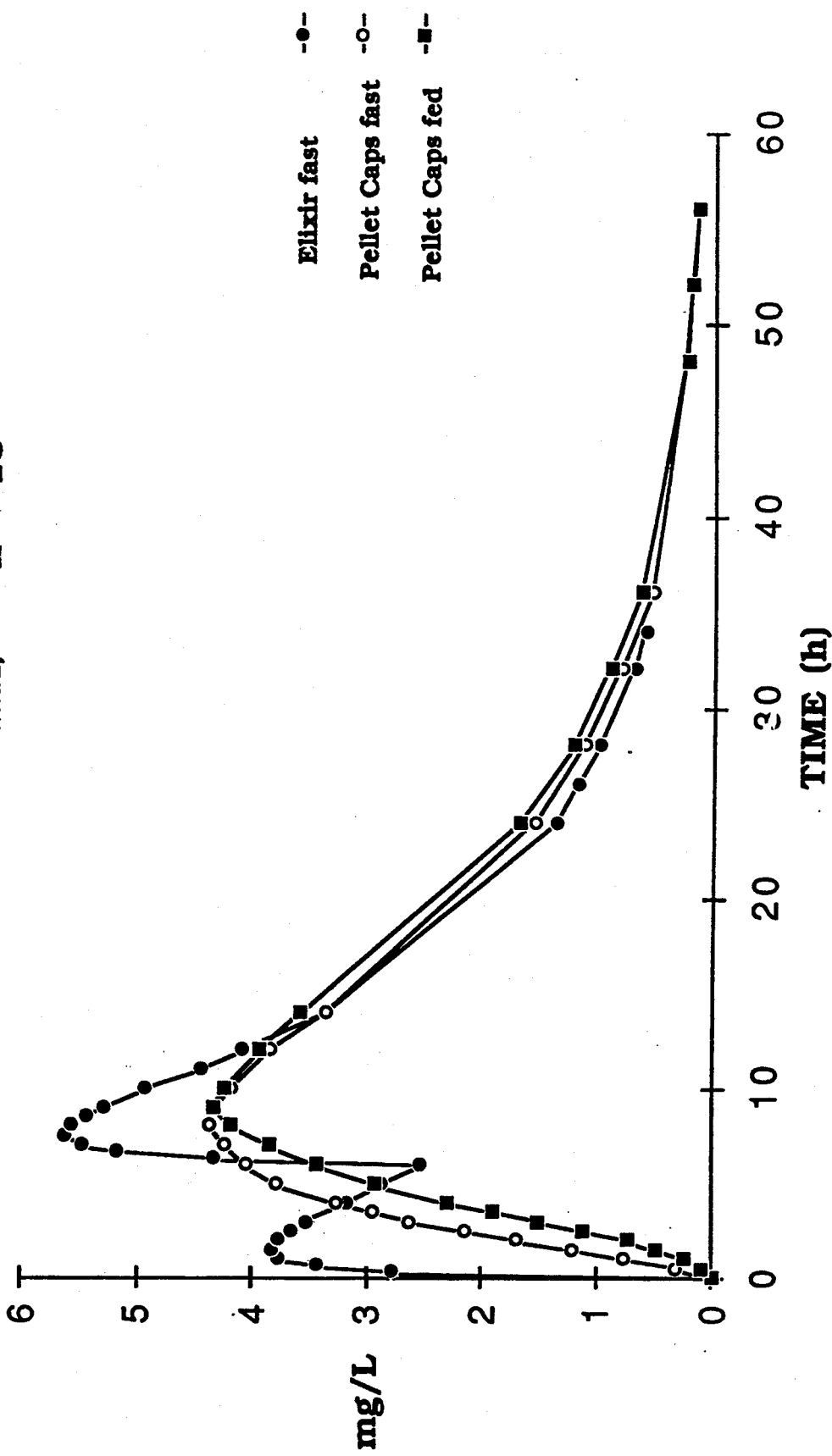
FIGURE 3: SINGLE DOSE BIOAVAILABILITY STUDY AVERAGE DATA, n = 18

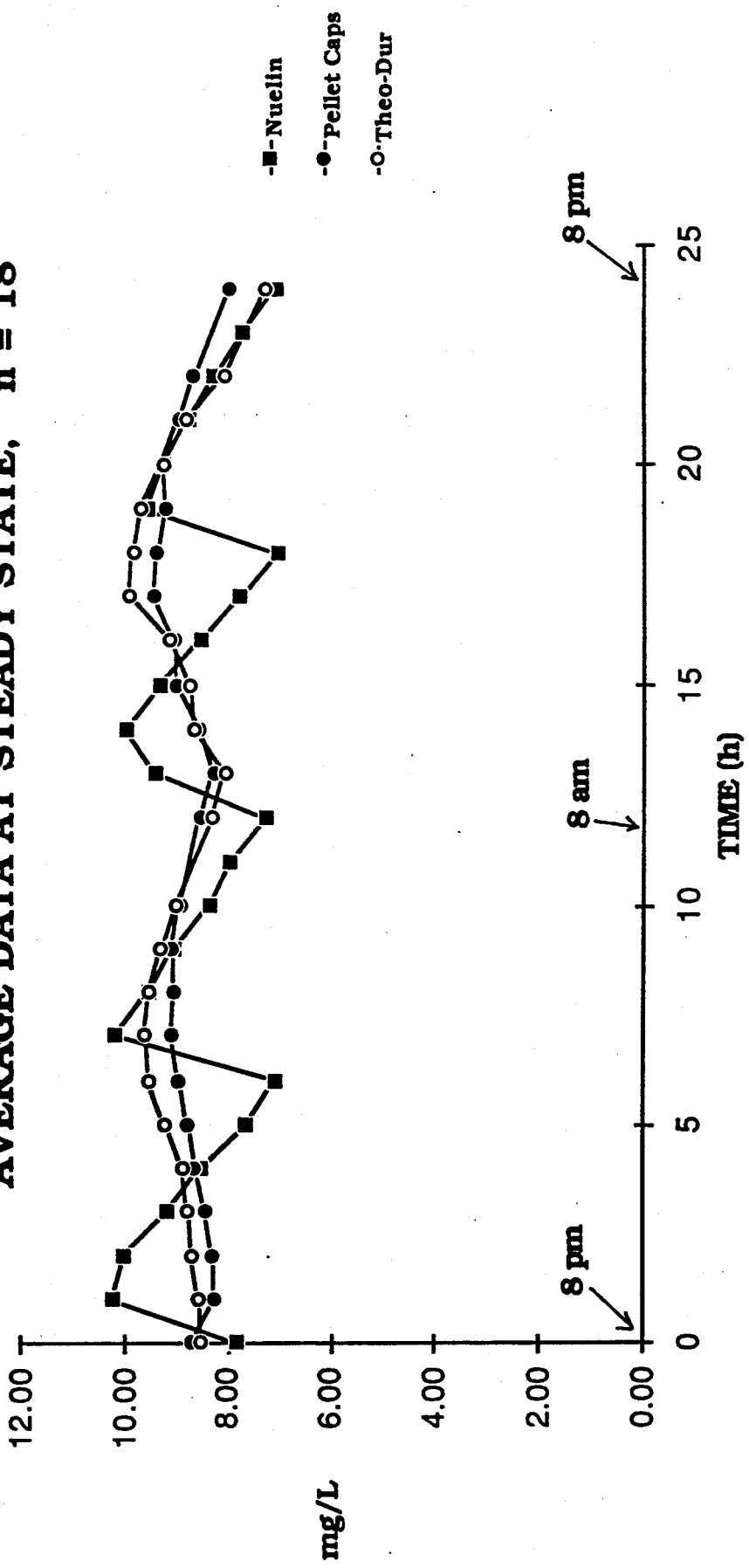
FIGURE 4: MULTIPLE DOSE BIOAVAILABILITY STUDY AVERAGE DATA AT STEADY STATE, n = 18

THEOPHYLLINE DOSAGE FORM

This is a continuation of application Ser. No. 457,198, filed Dec. 29, 1989, now abandoned.

The present invention relates to a pharmaceutical composition in particular a pharmaceutical composition including a theophylline compound and to a method for preparing same.

As is known in the prior art, 1,3-dimethylxanthine, is a naturally occurring xanthine derivative and has been used as a bronchodilator, cardiotonic, diuretic and respiratory stimulant for over sixty years. Bronchodilatation is the major therapeutic property of theophylline and is achieved by inducing relaxation in the smooth muscle of the bronchi. Therefore theophylline is commonly used to relieve bronchospasm associated with asthma and chronic obstructive airways disease (COAD).

Over the past twenty years the pharmacodynamics and pharmacokinetics of theophylline have been extensively investigated and a therapeutic plasma concentration range has been defined. In an attempt to maintain a constant concentration of theophylline within this range during chronic therapy, a number of prior art sustained release preparations have been marketed.

However, such prior art preparations still suffer from a number of disadvantages. Such disadvantages include the fact that the preparations may exhibit dose dumping or fluctuations in plasma theophylline concentrations which may increase the likelihood of toxicity. Moreover, some degree of diurnal variation in plasma theophylline concentrations have been noted. Further, bioavailability of prior art preparations may be compromised by food. This is important since complex dosage regimens may lead to non-compliance.

Accordingly, it is an object of the present invention to overcome, or at least alleviate, one or more of the difficulties related to the prior art.

Accordingly, in a first aspect of the present invention there is provided a pharmaceutical sustained release pellet composition including a core element including at least one active ingredient including a theophylline compound; and a core coating for the core element which is partially soluble at a highly acidic pH to provide a slow rate of release of theophylline compound and wherein the theophylline compound is available for absorption at a relatively constant faster rate in the intestine over an extended period of time.

Preferably, the core coating, in use, generates a dissolution profile for the pellet composition which is equal to or greater than the minimum dissolution required to provide substantial bioequivalence with a capsule or tablet containing the at least one active ingredient in a sustained release form.

By "sustained release pellet composition" we mean release of theophylline at such a rate that blood levels are maintained within the therapeutic range but below toxic levels over an extended period of time e.g. 12 to 24 hours or greater.

Desirably, for some applications of the invention, the rate of release at the less acidic to basic pH is greater than the rate of release at the highly acidic pH, preferably 1.2 to three times greater. In some applications, the rate of release of theophylline compound may be substantially zero at a highly acidic pH. Where some release of theophylline compound does occur in the stomach, this may occur at a relatively constant rate.

The pharmaceutical pellet composition according to the present invention may include a plurality of coated core elements.

The pharmaceutical pellet composition may be provided in any suitable unit dosage form. An encapsulated form may be used. The encapsulated pharmaceutical pellet composition may thus provide, in use, a blood profile in a patient to be treated which is substantially bio-equivalent to commercial capsules or tablets, including theophylline in a sustained release form, but reduces, or eliminates one or more of the difficulties of prior art formulations discussed above.

The pharmaceutical pellet composition may be provided in a tablet form. A tablet may be formed by compression of the pellets, optionally with the addition of suitable excipients.

A first dissolution profile may be measured at a pH level approximating that of the stomach. At least a second dissolution profile may be measured at pH levels approximating that of at least one point in the intestine.

A highly acidic pH may simulate the stomach and a less acidic to basic pH may simulate the intestine. By the term "highly acidic pH" as used herein we mean a pH in the range of approximately 1 to 4, by the term "less acidic to basic pH" we mean a pH of greater than 4 up to approximately 7.5, preferably approximately 6 to 7.5.

A pH of approximately 1.2 may be used to simulate the pH of the stomach.

A pH of approximately 6.0 to 7.5 preferably 7.5 may be used to simulate the pH of the intestine.

"Bio-equivalence" as used herein, means that the area under the curve (AUC) and Cmax from a plot of blood concentration of active ingredient versus time are within certain designated requirements by Health Authorities. For example the blood levels achieved may be plus or minus 20% in 80% or more of the subjects when compared to an equivalent product.

"Dissolution profile" as used herein, means a plot of amount of active ingredient released as a function of time. The dissolution profile may be measured utilising the Drug Release Test (724) which incorporates standard test USPXXII 1990. (Test(711)). A profile is characterised by the test conditions selected. Thus the dissolution profile may be generated at a preselected shaft speed, temperature and pH of the dissolution media.

It will be understood that since the theophylline compound is provided in a sustained release pellet form significantly less fluctuations in plasma theophylline concentrations at steady state over a 24 hour period are generated. This is expected to result in less toxic and more effective therapeutic activity.

Similarly, it has been found that the pharmaceutical pellet composition according to the present invention generates less diurnal variation and less peak to trough variations in plasma theophylline concentrations than prior art preparations.

Moreover, the pharmaceutical pellet composition according to the present invention shows no evidence of dose dumping. The bioavailability of the theophylline generated from the pharmaceutical pellet composition is not compromised by food so that compliance will improve as the product may be taken without regard to meals.

The theophylline compound in the pharmaceutical pellet composition may take any suitable form. The theophylline compound may be provided in an anhydrous or hydrous form. The theophylline compound may be provided in a salt form. By the term "theophylline compound", as used herein we mean a compound selected from theophylline and derivatives thereof and other xanthines and derivatives thereof. An ethylene diamine salt of theophylline may be used.

FIG. 1 shows the dissolution profile for the Pellet Composition B, defined hereafter.

FIG. 2 represents a dissolution profile for the Pellet Composition A, defined hereafter.

FIG. 3 is a graphic representation of a single dose bioavailability study for elixir pellet capsules according to the invention administered after feeding and after fasting as reported in Table 5.

FIG. 4 is a graphic representation of the multiple dose bioavailability study comparing theophylline pellet capsules according to the invention, Neulin ®, and Theo-Dur ® reported in Phase II of Example 2.

The active ingredient may be available for absorption even in regions of the gastrointestinal tract which are not sufficiently alkaline to dissolve the enteric core coating component.

Thus the active ingredient is available for absorption in an absorption region substantially immediately after the pyloric sphincter in the patient. Such an absorption region may generally be characterised by a pH between approximately 1.2 and 5.5.

Absorption will substantially occur in the small intestine but since absorption will continue over an extended period of time, then some absorption will occur additionally some way into the large intestine.

Accordingly, in a preferred aspect according to the present invention there is provided a sustained release pharmaceutical pellet composition including a core element including at least one active ingredient including a theophylline compound; and a hybrid core coating which coating provides a relatively constant low rate of release at a highly acidic pH and a relatively constant higher rate of release at a less acidic to basic pH over an extended period of time.

The hybrid core coating may include at least one insoluble matrix polymer;

at least one enteric polymer which is substantially insoluble at acidic pH but at least partially soluble at a less acidic to basic pH;

at least one component which is at least partially soluble at acidic pH.

It has been found necessary in order to achieve a slow rate of release at acidic pH of theophylline and a faster relatively constant rate of release over an extended period of time to include the above three components in the hybrid core coating.

Preferably the enteric polymer is readily soluble at a less acidic to basic pH.

Preferably the at least partially water soluble component is a readily water-soluble component.

Accordingly the hybrid core coating may include an effective amount of a matrix polymer which is substantially insoluble independent of pH an enteric polymer whose solubility is pH dependent, and an at least partially water soluble component.

The rate of dissolution at highly acidic pH of the hybrid core coating will depend on the amount of the at least partially water soluble component, and the thickness of the coating. Typical core coatings may be in the range of approximately 5 to 200 um, preferably approximately 40 to 80 um. It will be understood, accordingly, that the rate of absorption may be modified by modifying the thickness and/or the composition of the hybrid core coating.

Once a minimum amount of the at least one partially soluble component and/or the maximum thickness of the coating to achieve the minimum dissolution profile at an highly acidic pH has been established, then it is simply a matter of design choice to adjust the composition and/or thickness of coating as desired.

It has been found that by manipulating the partially acid soluble component, and the at least one enteric component, one can modify the release properties of the polymer coating. With theophylline as the active substance, dissolution is slow at an acidic pH and increases substantially at a less acidic to basic pH. Moreover, the dissolution rate may be controlled by modifying the concentration of the partially acid soluble and enteric component as well as the thickness of the polymer film.

Moreover, the dissolution rate may be controlled by modifying the concentration of the enteric polymer component in the hybrid core coating.

Accordingly in a preferred aspect the hybrid core coating may include approximately 10 to 95% based on the total weight of the hybrid core coating, excluding filler and plasticiser, of at least one insoluble matrix polymer selected from the group consisting of acrylic ester polymers, methacrylic ester polymers and mixtures thereof;

approximately 1 to 30% by weight based on the total weight of the hybrid core coating, excluding filler and plasticiser, of at least one enteric polymer selected from the group consisting of cellulose acetate phthalate, hydroxypropyl methyl-cellulose phthalate (HPMCP), polyvinyl acetate phthalate, methacrylic acid copolymer, hydroxypropyl methylcellulose acetate succinate, shellac, cellulose acetate trimellitate and mixtures thereof; and approximately 1 to 60% by weight based on the total weight of the hybrid core coating excluding filler and plasticiser of an at least partially acid soluble component selected from polyvinylpyrrolidone, hydroxypropyl cellulose, hydroxypropyl methylcellulose, polyethylene glycol having a molecular weight of from 1700 to 20,000, polyvinyl alcohol and monomers therefor and mixtures thereof.

Particularly preferred enteric polymers include synthetic resin bearing carboxyl groups. The methacrylic acid copolymer sold under the trade designation "Eudragit L30D" has been found to be suitable.

The at least one enteric polymer may be present in the coating in an amount of from approximately 1 to 30% by weight, preferably 2.5 to 10% by weight, based on the total weight of the hybrid core coating excluding weight of filler and plasticiser.

The at least partially acid-soluble component may preferably be selected from polymers such as polyethylene glycol, polyvinyl pyrrolidone, hydroxypropyl cellulose, hydroxypropyl methylcellulose or monomers such as sugars, salts, or organic acids and mixtures thereof.

The at least partially acid-soluble component may be present in the coating in amounts of from approximately 1 to 60%, preferably 20 to 40% by weight, based on the total weight of the hybrid core coating excluding weight of filler and plasticisers.

The at least one insoluble matrix polymer may preferably be selected from polymers or copolymers of acrylates or methacrylates having a low quaternary ammonium content may be used. The acrylic acid ethyl ester:methacrylic acid methyl ester (70:30) copolymer sold under the trade designation "Eudragit NE30D" has been found to be suitable.

The at least one insoluble matrix polymer may be present in the coating in an amount of from approximately 10 to 95% by weight preferably 40 to 70% by weight based on the total weight of the hybrid core coating excluding weight of filler and plasticiser.

Preferably the weight ratio of enteric polymer:insoluble matrix polymer:water soluble excipient is approximately 2.5:70:20 to 10:40:40.

The hybrid core coating may further include
at least one plasticiser; and optionally
at least one filler.

The hybrid core coating may preferably include
approximately 2.5 to 50% by weight based on the total weight of the hybrid core coating of at least one plasticiser selected from diethyl phthalate, triethyl citrate, triethyl acetyl citrate, triacetin, tributyl citrate, polyethylene glycol having a molecular weight of from 200 to less than 1700 and glycerol and the like; and
0 to approximately 75% by weight based on the total weight of the hybrid core coating of a filler selected from insoluble materials such as silicon dioxide, titanium dioxide, talc, alumina, starch, kaolin, polacrilin potassium, powdered cellulose, and microcrystalline cellulose and mixtures thereof.

It will be understood that the plasticiser used may be largely dictated by the polymer used in the coating formulation, and the solubility of the plasticiser in the coating media. The plasticiser may function to improve the physical stability of the pellet. A plasticiser is particularly preferred where the enteric polymer is of relatively low molecular weight. It should be noted that acid or water soluble plasticisers can also be used to function as the partially acid soluble component.

The plasticiser may be present in any suitable effective amount. Amounts of from approximately 25 to 50% by weight preferably 5 to 30% by weight based on the total weight of the hybrid core coating, excluding filler, have been found to be suitable.

Preferred hybrid core coating include

| (Insol. matrix) | Ethyl cellulose | 40-70% |
|---|---|---|
| (Enteric polymer) | Hydroxypropylmethyl cellulose phthalate | 2.5-10% |
| (Acid-soluble) | Polyethylene glycol | 20-40% |
| (Plasticiser) | Diethyl phthalate | 2.5-30% |
| | or | |
| (Insol. matrix) | Eudragit NE30D | 40-70% |
| (Enteric polymer) | Eudragit L30D | 2.5-10% |
| (Acid-soluble) | polyethylene glycol 6000 NF | 20-40% |
| (Plasticiser) | Triethylcitrate | 2.5-30% |

As stated above the hybrid core coating may further include at least one filler. The at least one filler may be selected from those insoluble fillers listed below for the manufacture of the core element.

The filler may be present in any suitable effective amount. Amounts of from 0 to approximately 75% by weight, preferably 0–50% by weight based on the total weight of the core coating have been found to be suitable.

In a preferred aspect of the present invention the core element of the pharmaceutical composition may include an effective amount of a theophylline compound;
at least one core seed; and
at least one binding agent.

The theophylline compound may be present in any suitable effective amount. The theophylline compound may be present in amounts of approximately 10 to 95% by weight, preferably approximately 20 to 90% by weight, based on the total weight of the core element. The binding agent may be present in amounts of from approximately 0 to 45% by weight preferably approximately 0 to 10% by weight based on the total weight of the core element.

The binding agent may be of any suitable type. Suitable binders may be selected from polyvinylpyrrolidone, hydroxypropyl cellulose, hydroxypropyl methylcellulose, methylcellulose and hydroxyethyl cellulose, sugars and mixtures thereof. The binding agent may be provided in the form of a granulating solution. An aqueous or organic solvent may be included. Methanol, ethanol or mixtures thereof may be used as solvents.

The size and amount of the core seed may vary substantially from approximately 425 um to 1700 um depending upon the amount of active ingredient to be included. Accordingly, the core seeds may vary from approximately 5 to 95% by weight, preferably 10 to 75% by weight based on the total weight of the core element. The core seed may be of such a diameter to provide a final core element having a diameter of approximately 500 to 2000 um.

The core seed may be of any suitable type. A sugar or an active core seed may be used.

The core element may further include other carriers or excipients, fillers, stabilizing agents and colorants. Suitable fillers may be selected from insoluble materials such as silicon dioxide, titanium dioxide, talc, alumina, starch, kaolin, polacrilin potassium, powdered cellulose, and microcrystalline cellulose and mixtures thereof. Soluble fillers may be selected from mannitol, sucrose, lactose, dextrose, sodium chloride, sorbitol and mixtures thereof.

The filler may be present in amounts up to approximately 75% by weight based on the total weight of the core element.

Typical core formulations may be prepared in the amounts as follows:

| Spheronisation | | |
|---|---|---|
| | Theophylline | 20-90% |
| | Core seeds | 10-75% |
| | hydroxypropyl cellulose | 0.1-10% |
| Extrusion | | |
| | Theophylline | 20-90% |
| (extrusion agent) | microcrystalline cellulose | 1-20% |
| | hydroxypropyl cellulose | 0.1-10% |
| (filler) | lactose | 0-60% |

The hybrid core coating composition may be provided in the form of a solution, dispersion or suspension.

The solvent may be present in amounts of from approximately 25 to 97% by weight based on the total weight of the hybrid core coating composition. The solvent for the polymer may be a solvent such as water, methanol, ethanol, methylene chloride and mixtures thereof.

The diluting medium may be present in amounts of from approximately 25 to 97% by weight based on the total weight of the hybrid core coating composition and is comprised predominantly of water.

Typical hybrid core coating formulations may be prepared in the amounts as follows:

| Core Coating Formulation | | |
|---|---|---|
| A. Insoluble matrix polymer | 40-70 | % excluding solvent |
| Enteric | 2.5-10 | |
| Acid soluble | 20-40 | |
| Plasticiser | 2.5-30 | |
| Solvent | 85-97% | of total coating formula. |
| B. For aqueous redispersion or suspension of polymers formulation A becomes: | | |
| Insoluble matrix polymer | 40-70 | % excluding solvent |
| Enteric | 2.5-10 | |
| Acid soluble | 20-40 | |
| Plasticiser | 2.5-30 | |
| Water | 75-97% | of total coating formula |

Sufficient plasticiser may be added to ensure film formation.

In a further aspect of the present invention, there is provided a pharmaceutical sustained release product in a unit dosage form including a plurality of pellets, each pellet including a core element including a theophylline compound; and a core coating for the core element which is partially soluble at a highly acidic pH and wherein the active ingredient is available for absorption at a relatively constant rate in the small intestine over an extended period of time.

Spray coating of core elements may be undertaken utilising bottom or top located spray nozzles. A bottom spray nozzle may reside proximate to the base of the fluidised bed facing upwards while a top spraying nozzle is located above the contents of the bed and facing downwards.

The method may include the preliminary steps of providing a theophylline compound;
at least one binding agent;
at least one core seed; and coating the core seeds with the theophylline compound and binding agent to form a core element.

In a preferred form the at least one binding agent is provided in a granulating solution. In this form the coating step may be conducted as a spheronisation process. The spheronisation process includes contacting the core seeds with the active ingredient and simultaneously adding the granulating solution thereto. The spheronisation process may be conducted in a spheronising machine.

In an alternative aspect of the present invention, the method according to the present invention may further include providing the active ingredient and binder in a solution or slurry of a solvent and spraying the core seeds with the solution or slurry. The spraying step may be conducted in a fluidised bed chamber.

In a further alternative aspect of the present invention, the method for preparing a core element may include providing a theophylline compound;
at least one binding agent; and
an effective amount of a solvent,
mixing the ingredients; and subjecting the ingredients to an extrusion followed by marumerisation to form a core element.

The solvent may be an aqueous or organic solvent or mixtures thereof. The solvent may be present in an amount effective to allow the ingredients to be extruded.

The core elements formed are then subjected to a drying step. The drying step may be conducted in a fluidised bed or drying oven.

The sustained release pharmaceutical pellet composition may be administered under a similar dosage regimen to that used in the prior art. The multi-pellet encapsulated form may for example be administered every twelve or twenty-four hours in sustained release forms.

The pharmaceutical pellet composition may be in multi-pellet encapsulated, sprinkle sachet or tableted forms.

In accordance with a further aspect of the present invention, there is provided a method of treating cardiotonic, diuretic or respiratory conditions in patients requiring such treatment which method includes administering to a patient an effective amount of a pharmaceutical sustained release pellet composition as described above.

It will be understood that the method of treating the abovementioned conditions according to this aspect of the present invention provides an advantage in reducing side effects associated with prior art sustained release products in a tablet or capsule form as described above. These side effects include headache, palpitation, dizzyness, nausea, hypotension, visual disturbance, insomnia, restlessness, confusion and diuresis.

The present invention will now be more fully described with reference to the accompanying examples. It should be understood, however, that the following description is illustrative only and should not be taken in any way as a restriction on the generality of the invention specified above.

EXAMPLE 1

| Spheronised Core Composition 1 | | |
|---|---|---|
| Theophyline | 25.0 kg | 75.7% |
| Sugar seeds | 7.5 kg | 22.7% |
| Hydroxypropyl cellulose (dissolved in methanol) | 0.52 kg | 1.6% |
| Extruded Core Composition 2 | | |
| Theophylline | 40.0 kg | 87% |
| microcrystalline cellulose | 4.0 kg | 8.7% |
| hydroxypropyl cellulose | 2.0 kg | 4.3% |
| water | as required | |
| Hybrid Core Coating Composition A | | |
| ethylcellulose N-100 | 104 g | 59.8% |
| polyethylene glycol 6000 NF | 50 g | 28.8% |
| hydroxypropylmethyl cellulose phthalate | 7.0 g | 4.0% |
| diethyl phthalate | 12.9 g | 7.4% |
| methanol | 1331 g | |
| methylene chloride | 1331 g | |
| Hybrid Core Coating Composition B | | |
| Eudragit NE30-D (as 30% dispersion in water) | 30.0 kg | 52.45% |
| Eudragit L30D (as 30% dispersion in water) | 2.5 kg | 4.37% |
| polyethylene glycol 6000 NF | 6.14 kg | 35.78% |
| triethyl citrate | 1.27 kg | 7.4% |
| talc | 15.9 kg | |
| water | 82.0 kg | |

Spheronised Core Manufacture

The sugar seeds were placed in a spheroniser. The sugar seeds were then coated with a dry mixture of the active ingredients and inactive excipients whilst concimittantly adding a solution of the binder components.

The wet cores so formed were then dried in a fluidised bed dryer for 1 hour.

Extruded Core Manufacture

The components of the extruded core composition were admixed to form an extrudable composition. The composition was then extruded through a side plate extruder and the extrudate marumerised to form wet cores.

The wet cores so formed were then placed in a fluid bed dryer for 1 hour.

Pellet Manufacture

The dried spheronised cores 1 and 2 were then placed in a fluid bed coating apparatus. The hybrid core coating compositions A and B were then sprayed onto the cores 1 and 2 to form pellets A and B respectively. At the conclusion of the process, the pellets were fluid bed dried.

A dissolution test was conducted on the pellet compositions A and B utilising the test method USPXXII 1990. (Test 711). A sample is dissolved in an aqueous medium previously degassed and equilibrated to 37° C. The media are USP pH 1.2 media without enzymes and pH 7.5 phosphate buffer. A sample of known volume is withdrawn at designated time intervals from the bath as directed and subjected to a suitable assay procedure. The mg of theophylline released as a function of time is plotted as the dissolution profile.

The tests were conducted at pH 1.2 and pH 7.5.

The baskets containing the samples were rotated at approximately 50 r.p.m. and the aqueous medium maintained at approximately 37° C.

The results are given in Tables 1 to 4 and FIGS. 1 and 2 herein. The results of pellet composition B at pH 1.2 and 7.5 are given in Tables 1 and 2 respectively. The hybrid coating on pellet composition A allows dissolution at pH 1.2, a significantly faster rate of dissolution is observed at pH 7.5. The results of pellet composition A at pH 1.2 and 7.5 are given in Tables 3 and 4 respectively, similar results to that obtained from composition A.

TABLE 1

DISSOLUTION DATA FOR PELLET COMPOSITION B MEASURED AT pH 1.2 (AVERAGED DATA FOR 6 SAMPLES)

| TIME MIN | MG RELEASED | (STD DEV) | % RELEASED | (STD DEV) |
|---|---|---|---|---|
| 60 | 30.33 | (1.56) | 9.87 | (0.41) |
| 120 | 62.16 | (2.71) | 20.23 | (0.68) |
| 180 | 88.21 | (3.77) | 28.70 | (0.92) |
| 240 | 111.77 | (4.43) | 36.37 | (1.09) |
| 300 | 135.11 | (5.48) | 43.96 | (1.26) |
| 360 | 156.50 | (3.91) | 50.93 | (0.67) |
| 420 | 179.85 | (6.80) | 58.52 | (1.54) |
| 480 | 201.55 | (5.87) | 65.59 | (1.12) |

TABLE 2

DISSOLUTION DATA FOR PELLET COMPOSITION B MEASURED AT pH 7.5 (AVERAGED DATA FOR 6 SAMPLES)

| TIME MIN | MG RELEASED | (STD DEV) | % RELEASED | (STD DEV) |
|---|---|---|---|---|
| 60 | 72.13 | (1.70) | 23.61 | (0.38) |
| 120 | 137.49 | (3.15) | 45.00 | (0.67) |
| 180 | 195.03 | (3.81) | 68.84 | (0.87) |
| 240 | 242.12 | (4.53) | 79.25 | (1.03) |
| 300 | 275.41 | (2.94) | 90.17 | (1.67) |
| 360 | 291.02 | (1.11) | 95.27 | (1.20) |
| 420 | 301.84 | (3.61) | 98.81 | (1.04) |

TABLE 2-continued

DISSOLUTION DATA FOR PELLET COMPOSITION B MEASURED AT pH 7.5 (AVERAGED DATA FOR 6 SAMPLES)

| TIME MIN | MG RELEASED | (STD DEV) | % RELEASED | (STD DEV) |
|---|---|---|---|---|
| 480 | 307.84 | (2.39) | 100.77 | (0.81) |

TABLE 3

DISSOLUTION DATA FOR PELLET COMPOSITION A MEASURED AT pH 1.2 (AVERAGED DATA FOR 3 SAMPLES)

| TIME MIN | MG RELEASED | (STD DEV) | % RELEASED | (STD DEV) |
|---|---|---|---|---|
| 60 | 29.91 | (0.98) | 9.71 | (0.31) |
| 120 | 60.21 | (2.19) | 19.55 | (0.69) |
| 180 | 90.78 | (1.88) | 29.48 | (0.58) |
| 260 | 132.35 | (2.97) | 42.98 | (0.93) |

TABLE 4

DISSOLUTION DATA FOR PELLET COMPOSITION A MEASURED AT pH 7.5 (AVERAGED DATA FOR 3 SAMPLES)

| TIME MIN | MG RELEASED | (STD DEV) | % RELEASED | (STD DEV) |
|---|---|---|---|---|
| 60 | 70.74 | (0.52) | 22.96 | (0.20) |
| 120 | 141.78 | (0.90) | 46.02 | (0.36) |
| 180 | 206.66 | (1.56) | 67.08 | (0.53) |
| 260 | 271.62 | (3.26) | 88.17 | (1.19) |

EXAMPLE 2

Clinical Trials

Phase I - Single Dose Study

Phase I was a three-way crossover single dose study to compare the relative bioavailability of Pellet Capsules according to the present invention with the reference product Elixophyllin ® elixir, a rapid release formulation demonstrated to be completely bioavailable. The effect of food on the bioavailability of Pellet Capsules was also examined.

Both products were administered to eighteen healthy, non-smoking, adult subjects. The subjects were randomized by weight into three equal size groups I, II and III. These groups were then randomly sorted into either regimens A, B or C.

All dosing regimens were administered after a twelve hour overnight fast, and regimen B was administered immediately after food.

A - Elixophyllin ® elixir (150 mg in 28 mL), administered with 152 mL water on two separate occasions six hours apart, to give a total of 300 mg of theophylline.

B - Pellet Capsules including pharmaceutical pellets according to the present invention, 300 mg of theophylline administered as a single dose with 180 mL of water immediately after the standard FDA recommended "high fat" breakfast.

C - Pellet Capsules including pharmaceutical pellets according to the present invention, 300 mg of theophylline administered as a single dose with 180 mL of water.

The washout period between each dosage regimen was one week.

Absorption

The results summarised in Table 5 indicate that the extent of absorption of Pellet Capsules taken fasting is equivalent to that of Elixophyllin ®, since statistical analysis (Analysis of Variance) of the parameter area under the curve ($AUC_{0-inf}$) shows no significant difference at p=0.05.

Bioavailability - Effect of food

The results summarised in Table 5 indicate that Pellet Capsules taken with food are absorbed to an equivalent extent when compared with both products taken fasting. This demonstrates that there is no reduction in the extent of absorption when Pellet Capsules are coadministered with a high fat meal and no evidence of dose dumping. When the formulation was coadministered with food, absorption was marginally delayed. This delay is of no relevance at steady state after multiple dosing.

The results summarised in Tables 5 and FIG. 3 indicate that Pellet Capsules fulfill the requirements of a sustained release product. While a single 300 mg dose of Pellet Capsules achieves a peak plasma concentration of 4.5 mg/L irrespective of the presence of food, the same dose of the reference product Elixophyllin ® would achieve a peak plasma concentration approximately twice that value. In addition the time taken to reach peak plasma concentration is longer for Pellet Capsules compared with Elixophyllin ®. This demonstrates that Pellet Capsules can provide therapeutic plasma theophylline concentrations within the defined narrow therapeutic concentration range with a decreased probability of theophylline toxicity due to lower peak to trough variations in blood levels.

In summary, this single dose study demonstrated the general sustained-release attributes of the Pellet Capsules theophylline formulation and highlighted the additional advantage of lack of food effect on the extent of theophylline absorption and decreased peak to trough variations in blood levels.

TABLE 5

Comparison of Pharmacokinetic parameters (mean ± SD) for single doses of theophylline obtained from 18 healthy subjects

| | REGIMEN | | | |
|---|---|---|---|---|
| PARA-METER | A Elix-ophyllin ® fasting | B Pellet Capsule as with food | C Pellet Capsule as fasting | STATIS-TICAL ANALYSIS |
| F % | — | 94.2 (11.5)[b] | 94.5 (17.0) | n.s.[a,c] |
| $AUC_{0-inf}$ mg.h/L | 97.1 (33.7) | 90.9 (31.3) | 91.2 (33.8) | n.s.[a] |
| Cpmax mg/L | 9.1[*d] (2.0) | 4.5 (1.0) | 4.5 (1.2) | A > B = C[e] |
| $t_{max}$ h | 1.3 (0.9) | 9.5 (1.7) | 8.0 (1.3) | B > C > A[d] |
| $t_{\geq 0.75 Cpmax}$ h | — | 8.0 (1.3) | 10.3 (3.5) | n.s.[f] |
| $t_{\frac{1}{2}}$ h | 7.6 (1.9) | 9.0 (1.4) | 8.9 (2.0) | A < B = C[a] |
| $Ke_2$ $h^{-1}$ | 0.10 (0.02) | 0.08 (0.02) | 0.08 (0.02) | A > B = C[a] |

[a]Analysis of Variance
[b]standard deviation
[c]not significant at p = 0.05
[d]Cpmax - for comparison the Elixophyllin is expressed as twice the value obtained following the first dose.
[e]Newman-Keuls Multiple Range Test for significance
[f]Student's Paired t-test Phase II - Multiple Dose Study Phase II was a three-way crossover multiple dose study to compare the plasma steady state theophylline concentrations produced by three different formulations; Pellet Capsule pelletised sustained release capsules, Theo-Dur ® sustained release tablets and Neulin ® tablets. Neulin ® is an immediate release theophylline product.

All products were administered to eighteen healthy, nonsmoking, adult subjects. The subjects were randomised using Elixophyllin ® clearance values and then randomly sorted into either regimens A, B or C. Each subject's dose was tailored using single dose study data to obtain steady state plasma theophylline concentrations of approximately 10 mg/L.

All dosing regimens were administered with 180 mL of water. The products were administered at equal dosing intervals for six days. The subjects consumed a Xanthine-free but otherwise unrestricted diet. Sampling commenced after five days of chronic dosing.

A - Neulin ® tablets administered four times a day (six hourly)
B - Pellet Capsule capsules administered twice a day (twelve hourly)
C - Theo-Dur ® tablets administered twice a day (twelve hourly).

Absorption

The results summarised in Table 6 indicate that the extent of theophylline absorption is comparable between the products Pellet Capsules, Theo-Dur ® and Neulin ® after multiple dosing. In addition, the bioavailability (F) of theophylline is comparable between the sustained release products Pellet Capsules and Theo-Dur ® relative to Neulin ®.

Twice Daily Dosing

The results summarised in FIG. 4 indicate that after steady state plasma theophylline concentrations were achieved, 75% of the peak plasma theophylline concentrations were maintained throughout the dosing interval. These prolonged values demonstrate a sustained period of therapeutic plasma theophylline concentration, indicating that no more than twice daily dosing is necessary with Pellet Capsules to achieve maintenance of plasma concentrations within the recommended therapeutic range.

Fluctuations

The efficacy and toxicity of theophylline is directly related to the plasma theophylline concentration. The optimum therapeutic concentration range is 5 to 20 mg/L (Hendeles and Weinberger, 1983). Thus theophylline has a narrow therapeutic index. Plasma concentrations below 5 mg/L generally result in less than optimal bronchodilatation while concentrations above 20 mg/L are often associated with theophylline toxicity.

Theophylline is used prophylactically in the management of asthma and chronic obstructive airways disease (COAD), requiring continuous theophylline therapy for prolonged periods of time. When Pellet Capsules are administered at the appropriate dosing rate, the plasma theophylline concentrations observed are maintained within the defined therapeutic range.

The results summarised in Tables 6, 7 and 8 indicate that over a twenty four hour period, Pellet Capsules exhibit significantly less fluctuation (percentage fluctuation) in steady state plasma theophylline concentration compared to Theo-Dur ®. This demonstrates that Pellet Capsules achieve more reliable plasma theophylline concentrations within the therapeutic range and is a more reliable sustained-release theophylline product.

Diurnal Variation

Analysis of the percentage fluctuation at steady state plasma theophylline concentrations (Student's paired t-test) (Tables 6, 7 and 8) reveals that there is less diurnal variation in plasma theophylline concentrations when Pellet Capsules are compared with Theo-Dur ®. There is no difference in the extent of fluctuation during a twelve hour dosage interval either during the day or during the night with Pellet Capsules. In contrast, Theo-Dur ® exhibits significantly more fluctuation in plasma theophylline concentration during the day than during the night. Pellet Capsules exhibit less fluctuation in plasma theophylline concentration during the day compared to Theo-Dur ® although the extent of fluctuation during the night is comparable between the two sustained release products. These results confirm the diurnal variation reported in the literature for other commercially available products (Reed et al., 1986) and emphasise that Pellet Capsules is an improved formulation.

The multiple dose study confirms the results of the single dose study and highlights the additional advantages of significantly less diurnal variation as percent fluctuations in plasma theophylline concentrations at steady state.

TABLE 6

Steady state pharmacokinetic parameters (mean ± SD) for theophylline following administration of 3 theophylline preparations to 18 healthy subjects

| PARAMETER | REGIMEN A NEULIN ® | REGIMEN B PELLET CAPSULES | REGIMEN C THEO-DUR ® | STATISTICAL ANALYSIS |
|---|---|---|---|---|
| F% | — | 102.3 (14.4)[b] | 103 (11.2) | n.s.[a,c] |
| AUC TOTAL 24 hr mg.h/L | 208.7 (31.7) | 211.8 (33.3) | 214.3 (37.1) | n.s.[d] |
| % FLUCTUATION day[e] | 54.0 (16.0) | 26.3 (10.5) | 44.8 (15.3) | A > C > B[d] B C[a] |
| % FLUCTUATION night | 58.5 (19.5) | 25.8 (9.1) | 33.9 (10.5) | A > C = B[d] n.s.[a] |
| % FLUCTUATION total | 66.5 (18.9) | 36.7 (13.7) | 53.1 (14.1) | A > C > B[d] B C[a] |
| $Cp_{min}$ day mg/L | 6.9 (1.3) | 7.8 (1.5) | 7.2 (1.3) | B > C = A[d] |
| $Cp_{min}$ night mg/L | 7.0 (1.3) | 7.7 (1.4) | 7.8 (1.3) | A < B = C[d] |
| $Cp_{max}$ day mg/L | 10.5 (1.8) | 9.8 (1.6) | 10.4 (1.9) | n.s.[d] |
| $Cp_{max}$ night mg/L | 10.9 (1.4) | 9.6 (1.3) | 10.4 (2.1) | B < C = A[d] |
| $t \geq 0.75 CPmax$ h (day) | — | 11.7 (.06) | 9.7 (2.1) | B > C[a] |
| $t \geq 0.75 CPmax$ h (night) | — (0.4) | 11.8 (1.4) | 10.9 | B > C[a] |

[a] Student's paired t-test
[b] standard deviation
[c] not significant at p = 0.05
[d] Analysis of Variance
[e] % Fluctuation =

$$\frac{\text{Peak concentration} - \text{minimum concentration}}{\text{minimum concentration}} \times 100$$

TABLE 7

Comparison of the mean (±SD) values for the day and night time intervals at steady state plasma theophylline concentrations obtained from 18 healthy subjects.

| PARAMETER | PRODUCT | DAY 8 a.m.–8 p.m. | NIGHT 8 p.m.–8 a.m. | STATISTICAL ANALYSIS[a] |
|---|---|---|---|---|
| AUC mg.h/L | Pellet Caps | 106.7 (18.8)[b] | 105.1 (15.6) | n.s.[c] |
| | Theo-Dur ® | 106.0 (18.1) | 108.4 (20.4) | n.s. |
| % FLUCT. steady-state | Pellet Caps | 26.3 (10.5) | 25.8 (9.1) | n.s. |
| | Theo-Dur ® | 44.8 (15.3) | 33.9 (10.5) | day > night |
| $Cp_{max}$ mg/L | Pellet Caps | 9.8 (1.6) | 9.6 (1.3) | n.s. |
| | Theo-Dur ® | 10.4 (1.9) | 10.4 (2.1) | n.s. |
| $Cp_{min}$ mg/L | Pellet Caps | 7.8 (1.5) | 7.7 (1.4) | n.s. |
| | Theo-Dur ® | 7.2 (1.3) | 7.7 (1.3) | night > day |
| $t \geq 0.75$ $Cp_{max}$h | Pellet Caps | 11.7 (0.6) | 11.8 (0.4) | n.s. |
| | Theo-Dur ® | 9.7 (2.1) | 10.9 (1.4) | n.s. |

[a] student's paired t-test
[b] standard deviation
[c] not significant at p = 0.05

TABLE 8

Comparisons of the number of subjects and fluctuations of plasma theophylline concentrations for the sustained-release products at steady-state.

| Time (h) | Fluctuation (%) | Pellet capsules | Theo-Dur ® tablets |
|---|---|---|---|
| 0–24 (night/day) | <30 | 6 | 1 |
| | 30–40 | 8 | 1 |
| | 40–50 | 1 | 7 |
| | >50 | 3 | 9 |
| 0–12 (night) | <30 | 11 | 7 |
| | 30–40 | 6 | 4 |
| | 40–50 | 1 | 7 |

TABLE 8-continued

Comparisons of the number of subjects and fluctuations of plasma theophylline concentrations for the sustained-release products at steady-state.

| Time (h) | Fluctuation (%) | Number of subjects | |
|---|---|---|---|
| | | Pellet capsules | Theo-Dur ® tablets |
| | >50 | 0 | 0 |
| 12-24 | <30 | 13 | 2 |
| (day) | 30-40 | 3 | 4 |
| | 40-50 | 2 | 7 |
| | >50 | 0 | 5 |

Finally, it is to be understood that various other modifications and/or alterations may be made without departing from the spirit of the present invention as outlined herein.

I claim:

1. A pH-dependent sustained release pharmaceutical pellet composition for administration to a patient at a predetermined dosage and interval which comprises: a core element containing a therapeutically effective amount of methylated xanthine or a salt thereof as the active ingredient and a coating on said core element which comprises the following components:
   (a) at least 40% of a matrix polymer which is insoluble at a pH of from 1 to 7.5 and contributes to the control of the rate of release of the active ingredient in the stomach and intestines;
   (b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
   (c) from 1 to 60% of a compound soluble at a pH of from 1 to 4, sufficient to enable initiation of release of the active ingredient in the stomach; said percentages being by weight based on total weight of components (a), (b), and (c); the ratio of the components (a), (b), and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of said active ingredient over the course of said predetermined interval, said coated core element having a diameter of from 510 to 2400 microns.

2. A sustained release pharmaceutical pellet composition according to claim 1, wherein the methylated xanthine salt is an ethylene diamine salt of theophylline.

3. The sustained release pharmaceutical pellet composition of claim 1 wherein the rate of release in the intestine is 1.2 to 3 times greater than the rate of release in the stomach.

4. The sustained release pharmaceutical pellet composition of claim 1 wherein the active ingredient has a first dissolution profile measured at a pH of from 1 to 4, and a second dissolution profile measured at a pH of about 7.5 and wherein said first and second dissolution profile are each at least equal to the minimum dissolution required to provide substantially the same bioavailability as with an immediate release oral dosage form.

5. The sustained release pharmaceutical pellet composition of claim 1 wherein the core coating contains:
   as component (a), ethyl cellulose, a quaternary ammonium acrylic or methacrylic polymer, an acrylic or a methacrylic ester copolymer or a mixture thereof;
   as component (b), cellulose acetate phthalate, hydroxypropyl methylcellulose phthalate, polyvinyl acetate phthalate, methacrylic acid:acrylic acid ester copolymer, hydroxypropyl methylcellulose acetate succinate, shellac, cellulose acetate trimellitate and mixtures thereof; and
   as component (c), polyvinylpyrrolidone, hydroxypropyl cellulose, hydroxypropyl methylcellulose, polyethylene glycol having a molecular weight of from 1700 to 20,000, polyvinyl alcohol and monomers therefor and mixtures thereof.

6. A sustained release pharmaceutical pellet composition according to claim 5 wherein the core element has a formulation

| Theophylline | 20 to 90% by weight |
|---|---|
| Hydroxypropylcellulose | 0.1 to 10% by weight |
| Microcrystalline cellulose | 1 to 20% by weight |
| Lactose | 0 to 60% by weight. |

7. The sustained release pharmaceutical pellet composition of claim 5 wherein the core coating comprises:
   40 to 70% by weight of component (a);
   2.5–10% by weight of component (b); and
   20–40% by weight of component (c).

8. The sustained release pharmaceutical pellet composition of claim 5 wherein the core coating also includes up to 75% of a filler selected from silicon dioxide, titanium dioxide, talc, alumina, starch, kaolin, polacrilin potassium, powdered cellulose and microcrystalline cellulose and mixtures thereof and from 2.5 to 50% of plasticizer selected from diethyl phthalate, triethyl citrate, triethyl acetyl citrate, triethyl acetin, tributyl citrate, polyethylene glycol or glycerol, said percentages being based on the total weight of the core coating.

9. The sustained release pharmaceutical pellet composition of claim 5 wherein the rate of release in the intestine is 1.2 to 3 times greater than the rate of release in the stomach.

10. A sustained release pharmaceutical pellet composition according to claim 8 wherein the core coating contains:

| Ethyl cellulose | 40 to 70% |
|---|---|
| Hydroxypropylmethyl cellulose phthalate | 2.5 to 10% |
| Polyethylene glycol | 20 to 40% |
| Diethyl phthalate | 2.5 to 30% |

11. A sustained release pharmaceutical pellet composition according to claim 8 wherein the core coating contains:

| Eudragit NE30D | 40–70% |
|---|---|
| Eudragit L30D | 2.5–10% |
| polyethylene glycol 6000 NF | 20–40% |
| Triethylcitrate | 2.5–30% |

12. A method for treating cardiotonic, diuretic or respiratory conditions in a patient which comprises administering to said patient at a predetermined dosage and interval a pH-dependent sustained release pharmaceutical pellet composition which comprises: a core element containing a therapeutically effective amount of methylated xanthine or a salt thereof as the active ingredient and a coating on said core element which comprises the following components:
(a) at least 40% of a matrix polymer which is insoluble at a pH of from 1 to 7.5 and contributes to the control of the rate of release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach; said percentages being by weight based on total weight of components (a), (b), and (c); the ratio of the components (a), (b), and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of said active ingredient over the course of said predetermined interval, said coated core element having a diameter of from 510 to 2400 microns.

13. A pH-dependent sustained release pharmaceutical pellet composition for administration to a patient at a predetermined dosage and interval which comprises: a core element containing a therapeutically effective amount of methylated xanthine or a salt thereof as the active ingredient and a coating on said core element which comprises the following components:
(a) at least 40% of a matrix polymer which is insoluble at a pH of from 1 to 7.5 and is composed of ethyl cellulose, a quaternary ammonium acrylic or methacrylic polymer, an acrylic or a methacrylic ester copolymer or a mixture thereof which contributes to the control of the release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach; said percentages being by weight based on total weight of components (a), (b), and (c); the ratio of the components (a), (b), and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of said active ingredient over the course of said predetermined interval, said coated core element having a diameter of from 510 to 2400 microns.

14. A method for treating cardiotonic, diuretic or respiratory conditions in a patient which comprises administering to said patient at a predetermined dosage and interval a pH-dependent sustained release pharmaceutical pellet composition which comprises: a core element containing a therapeutically effective amount of methylated xanthine or a salt thereof as the active ingredient and a coating on said core element which comprises the following components:
(a) at least 40% of a matrix polymer which is insoluble at a pH of from 1 to 7.5 and is composed of ethyl cellulose, a quaternary ammonium acrylic or methacrylic polymer, an acrylic or a methacrylic ester copolymer or a mixture thereof which contributes to the control of the release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach; said percentages being by weight based on total weight of components (a), (b), and (c); the ratio of the components (a), (b), and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of said active ingredient over the course of said predetermined interval, said coated core element having a diameter of from 510 to 2400 microns.

* * * * *